US008687554B2

(12) United States Patent  (10) Patent No.: US 8,687,554 B2
Simons et al.  (45) Date of Patent: Apr. 1, 2014

(54) SYSTEM AND METHOD FOR SIMPLE PAIRING OF WIRED AND WIRELESS HEALTHCARE DEVICES TO A GATEWAY

(75) Inventors: David Peter Louis Simons, Veldhoven (NL); Frank Wartena, Eindhoven (NL); Robbert J. Mulder, Diessen (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/119,190

(22) PCT Filed: Sep. 10, 2009

(86) PCT No.: PCT/IB2009/053966
§ 371 (c)(1),
(2), (4) Date: Apr. 28, 2011

(87) PCT Pub. No.: WO2010/035165
PCT Pub. Date: Apr. 1, 2010

(65) Prior Publication Data
US 2012/0155387 A1    Jun. 21, 2012

(51) Int. Cl.
*H04W 4/00*  (2009.01)
(52) U.S. Cl.
USPC ........................................................ 370/328
(58) Field of Classification Search
USPC ........................................................ 370/328
See application file for complete search history.

(56) References Cited

U.S. PATENT DOCUMENTS

| 2001/0030950 | A1* | 10/2001 | Chen et al. ................ 370/329 |
| 2002/0159419 | A1 | 10/2002 | Morris |
| 2004/0090661 | A1 | 5/2004 | Nicolaescu |
| 2005/0086389 | A1 | 4/2005 | Chang |
| 2006/0020723 | A1 | 1/2006 | Chia-Chun |
| 2007/0088521 | A1* | 4/2007 | Shmueli et al. ............. 702/127 |
| 2007/0255597 | A1 | 11/2007 | Weispfenning et al. |

FOREIGN PATENT DOCUMENTS

| EP | 1862112 | 12/2007 |
| WO | WO0177980 | 10/2001 |

OTHER PUBLICATIONS

IEEE, Standards and Emerging Technologies, Continua: An Interoperable Personal Healthcare Ecosystem, Randay Carroll, Oct.-Dec. 2007, pp. 90-94.*

* cited by examiner

*Primary Examiner* — Mark Rinehart
*Assistant Examiner* — Maharishi Khirodhar

(57) ABSTRACT

A system and method for effecting communication between a plurality of healthcare measurement devices and a remote patient monitoring server is disclosed. In one embodiment, a method of effecting communication between the healthcare measurement devices and the remote patient monitoring server, includes communicating with an healthcare gateway device using a common gateway protocol to receive translated data via a plurality of translation units associated with a plurality of device communication modules residing in wired and wireless healthcare measurement devices, and communicating with the remote patient monitoring server using a plurality of remote protocols residing in a plurality of remote communication modules to transmit the received translated data. In some embodiments, the healthcare gateway device is communicatively coupled between the healthcare management devices and the remote patient monitoring server.

11 Claims, 3 Drawing Sheets

US 8,687,554 B2

SYSTEM AND METHOD FOR SIMPLE PAIRING OF WIRED AND WIRELESS HEALTHCARE DEVICES TO A GATEWAY

FIELD OF THE INVENTION

The present invention relates generally to remote and home healthcare systems, also known as telehealth and telecare systems, and in particular, to a system and method for pairing of healthcare measurement devices to a gateway.

BACKGROUND

Typically, connectivity between home healthcare measurement devices such as a weighing scale, a blood-pressure (BP) meter, and the like, and a home healthcare gateway device such as a settop box, mobile phone, personal digital assistant (PDA), personal computer (PC), and the like is either wired or wireless using a wide range of technologies. From a multivendor perspective, the wired connections can include technologies, such as a Universal Serial Bus (USB) cable, an RS232, an Ethernet, FireWire and so on, and the wireless connections can include technologies, such as Bluetooth, Zigbee, Wireless USB and so on and would be desirable to provide support for all these types of connections or to support as many device types as possible. For an application on the healthcare gateway device, to use the above wired and wireless connections and the attached healthcare measurement devices, software must be present on the healthcare gateway device which is aware of the above various types of connections; that is, which runs the connection protocol layers and is able to support such connections between the healthcare gateway device and healthcare measurement devices. For example, for the healthcare gateway device to use a Bluetooth enabled peripheral device, software must be present on the healthcare gateway device which is "Bluetooth aware"; that is, which runs the Bluetooth protocol layers to support a Bluetooth based connection between the healthcare gateway device and the healthcare measurement device. The conventional means of doing this is to provide software components called "device drivers" for the healthcare gateway device. Each healthcare measurement device with its associated type of wired or wireless connection may need a separate device driver installed on the healthcare gateway device to provide the functionality.

However, the difficulties with device drivers are well known. Device drivers are specific to operating systems and often to a particular version of an operating system. In addition, device drivers may be difficult to install and can interact undesirably with each other. Also, resource constraints of the healthcare gateway device may prevent inclusion of the multiple device drivers.

On the other hand, the recent advent of the USB has spurred operating system manufacturers to provide similar drivers for common peripherals and attached to a PC via a USB port. On Windows-based PCs, for example, these drivers are "plug and play"; Windows detects an attachment of a device to a USB port and automatically installs the appropriate driver. Unfortunately, the plug and play capability of the Windows environment has heretofore not been extended to remote and home healthcare systems and home healthcare measurement devices over wired and wireless links. There is also a trend in the Continua Health Alliance towards restricting to a single wired connection, such as USB and/or a single wireless technology, such as Bluetooth.

SUMMARY OF THE INVENTION

A system and method for a transport-agnostic gateway including a single type of plug-and-play ports for connecting wired and wireless healthcare measurement devices is disclosed. According to an aspect of the subject matter, a method for effecting communication between a plurality of healthcare measurement devices and a remote patient monitoring server, includes communicating with an healthcare gateway device using a common gateway protocol to receive translated data via a plurality of translation units associated with a plurality of device communication modules residing in wired and wireless healthcare measurement devices, and communicating with the remote patient monitoring server using a plurality of remote protocols residing in a plurality of remote communication modules to transmit the received translated data. In some embodiments, the healthcare gateway device is communicatively coupled between the healthcare management devices and the remote patient monitoring server. Further, communicating with the plurality of healthcare measurement devices includes detecting a type of the healthcare measurement device and connecting to the healthcare measurement device in accordance with the common gateway protocol.

The method further includes translating data received from the healthcare measurement devices in accordance with a plurality of device protocols into translated data adapted for the healthcare gateway device in accordance with the common gateway protocol. The method also includes translating information received from the healthcare gateway device in accordance with the common gateway protocol into translated information adapted for the one of the healthcare measurement devices in accordance with one of the device protocols. In some embodiments, translating includes selecting a translation routine from a set of predefined translation routines based upon the type of the healthcare measurement devices.

The methods, systems, and apparatuses disclosed herein may be implemented in any means for achieving various aspects, and may be executed in a form of a machine-readable medium embodying a set of instructions that, when executed by a machine, cause the machine to perform any of the operations disclosed herein. Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

A system and method for a transport-agnostic gateway including a single type of plug-and-play ports for connecting wired and wireless healthcare measurement devices is disclosed. In the following description, for purposes of explanation, numerous specific details are set forth in order to provide a thorough understanding of the various embodiments. It will be evident, however, to one skilled in the art that the various embodiments may be practiced without these specific details.

The terms "home healthcare gateway device", and "healthcare gateway device" are used interchangeably throughout the document.

Figure 1:
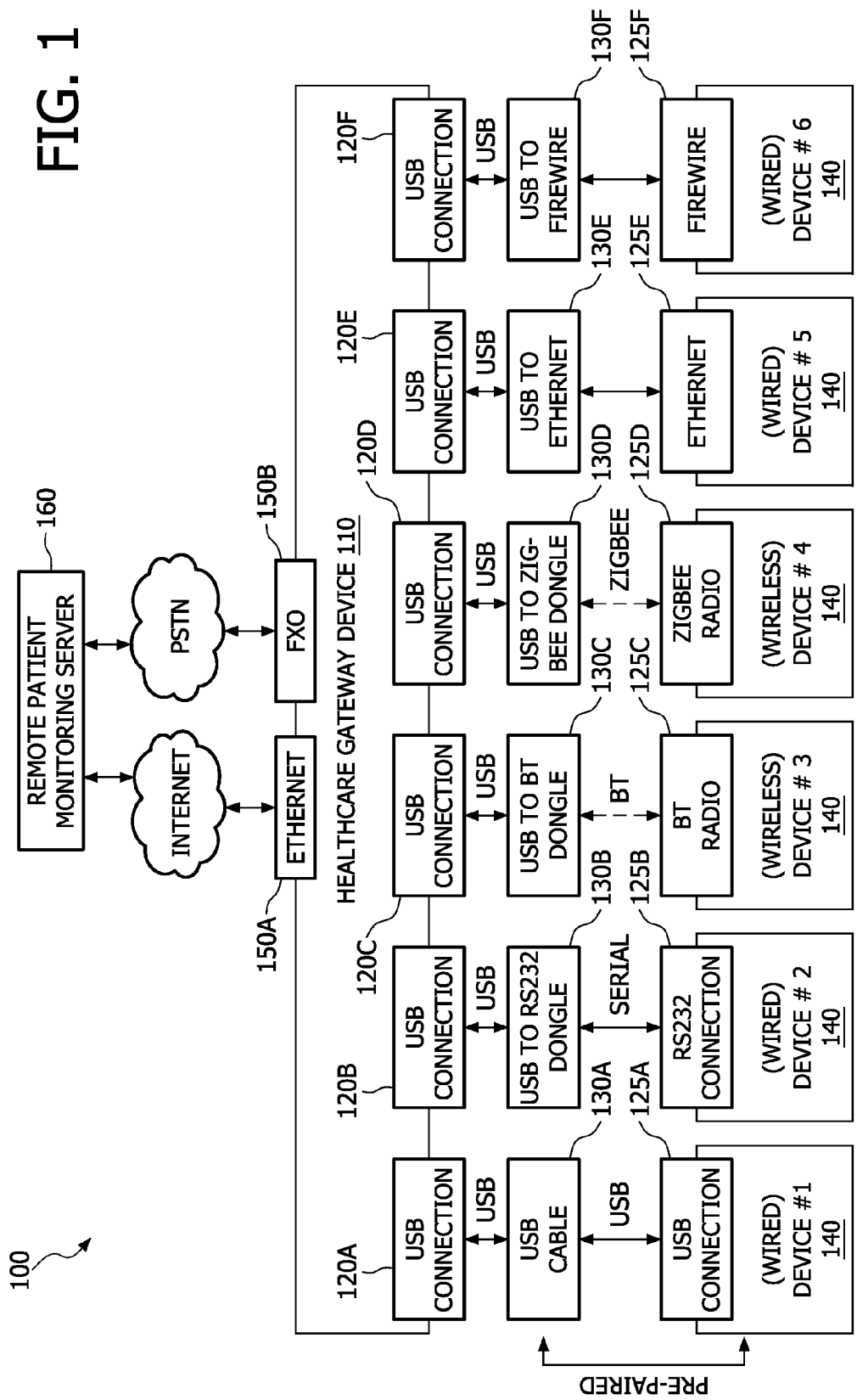
FIG. 1 illustrates a block diagram of a transport-agnostic gateway for connecting wired and wireless healthcare measurement devices, in accordance with an embodiment of the invention.

FIG. 1 illustrates a block diagram 100 of a transport-agnostic gateway for connecting wired and wireless healthcare measurement devices 140 to an healthcare gateway device 110, in accordance with an embodiment of the invention. Particularly, FIG. 1 illustrates the healthcare gateway device 110, a plurality of gateway communication modules 120A-N (hereinafter referred as the gateway communication modules 120), such as a plurality of USB connections, a plurality of device communication modules 125A-N (hereinafter referred as the device communication modules 125), a plurality of translation units 130A-N (hereinafter referred as the translation units 130), the plurality of wired and wireless healthcare measurement devices #1-N 140 (hereinafter referred as the healthcare measurement devices 140), a plurality of remote communication modules 150A-N (hereinafter referred as the remote communication modules 150), and a remote patient monitoring server 160.

The healthcare gateway device 110 effects transport-agnostic communication between the healthcare measurement devices 140 and the remote patient monitoring server 160. For example, the healthcare gateway device 110 may be a personal computer, a settop box, a mobile phone, a personal digital assistant, and the like.

As shown in FIG. 1, the healthcare gateway device 110 is communicatively coupled to the remote patient monitoring server 160 via a plurality of remote protocols residing in the remote communication modules 150 (e.g., Ethernet and FXO as shown in FIG. 1). As illustrated in FIG. 1, the remote communication modules 150 are communicatively coupled to the remote patient monitoring server 160 through a network (e.g., the Internet, PSTN). In these embodiments, the healthcare gateway device 110 includes the gateway communication modules 120 that use a common gateway protocol, and the remote protocols are compliant with the common gateway protocol. In some embodiments, the common gateway protocol is a USB protocol and the translation units 130 are connected to USB ports of the healthcare gateway device 110.

Further, the healthcare gateway device 110 includes the gateway communication modules 120 for communicating with the healthcare gateway device 110 using the common gateway protocol to receive translated data via the translation units 130 associated with the device communication modules 125 residing in the wired and wireless healthcare measurement devices 140.

The healthcare gateway device 110 also includes the remote communication modules 150 communicatively coupled to the gateway communication modules 120 to transmit the translated data to the remote patient monitoring server 160. Further, the remote communication modules 150 are communicatively coupled to the gateway communication modules 120 to receive the translated data from the remote patient monitoring server 160.

Further as shown in FIG. 1, the healthcare measurement devices 140 include the device communication modules 125. The device communication modules 125 may include peripheral detection and connection modules. In these embodiments, the plurality of device communication modules 125 transmit information to, and receive data from, the healthcare measurement devices 140 in accordance with a plurality of device protocols.

In some embodiments, the data from the healthcare measurement devices is transmitted to the translation units 130 using the device protocols such as a USB protocol, an RS232 protocol, an IR protocol, an Ethernet protocol, a FireWire protocol, a Bluetooth protocol, a Zigbee protocol, an ULP Bluetooth protocol, and a Z-Wave protocol.

In one example embodiment, the healthcare measurement devices 140 include devices such as a weigh scale and a BP-cuff, a glucometer, a thermometer, a heart rate sensor, an ECG sensor, an EEG sensor, an oximeter, a PT-INR sensor, a peak flow sensor, a spirometer, a respiration sensor, a passive infrared (PIR) motion sensor, a smoke detector, an emergency button and the like.

In another example embodiment, the device communication modules 125 residing in the wired and wireless healthcare measurement devices 140 include modules such a USB connection, an RS232 connection, an InfraRed (IR) connection, an Ethernet connection, a FireWire connection, a Bluetooth interface, a Wireless USB, a Zigbee interface, an Ultra Low Power (ULP) Bluetooth interface, a Z-Wave interface and the like.

Further as shown in FIG. 1, the translation units 130, operatively connected to the device communication modules 125 and to the gateway communication modules 120, translates the data received from the wired and wireless healthcare measurement devices 140 in accordance with the plurality of device protocols into translated data adapted for the healthcare gateway device 110 in accordance with the common gateway protocol. Further, the translation units 130 are operative to translate information received from the healthcare gateway device 110 in accordance with the common gateway protocol into translated information adapted for the plurality of wired and wireless healthcare measurement devices in accordance with the plurality of device protocols.

In the example embodiment illustrated in FIG. 1, the healthcare gateway device 110 includes only one type of wired plug-and-play ports, i.e., USB ports. Further, the healthcare gateway device 110 includes sufficient number of USB ports to accommodate a number of healthcare measurement devices 140 based on requirement. Further, in case of a USB realization, a USB hub is used to increase the number of USB ports. FIG. 1 illustrates a common transport and data-control model for healthcare measurement devices 140 (e.g., home healthcare measurement devices). Also, a generic Continua driver (i.e., the translation units 130 such as USB cable, USB to RS232 dongle, USB to BT dongle, USB to Zigbee dongle, USB to Ethernet, and USB to FireWire as illustrated in FIG. 1) can be developed and shipped along with the healthcare gateway device 110 to accommodate all dongles and the healthcare measurement devices 140.

In one example embodiment illustrated in FIG. 1, the wired Continua devices such as device #1 of the healthcare measurement devices 140, with the appropriate wired connectivity technology (e.g., a USB), can be readily plugged into the healthcare gateway device 110. Therefore, association of the healthcare measurement device 140 (e.g., device #1) to the appropriate gateway communication module (e.g., by plugging physically) is easy and unmistakable.

In another example embodiment illustrated in FIG. 1, for the wired Continua devices such as device #2 of the healthcare measurement devices 140, with another wired connectivity technology (e.g. an RS232 serial), a converter is supplied with the translation units 130 (e.g. a USB to an RS232 dongle). As a result, the healthcare measurement device 140

(e.g., device #2) can be associated unmistakably with the appropriate healthcare gateway device 110 by plugging in physically into one of the standard USB ports of the healthcare gateway device 110.

In yet another example embodiment illustrated in FIG. 1, the wireless devices, such as device #3 and device #4 of the healthcare measurement devices 140, are shipped with a pre-paired wireless dongle (i.e., the dongle to which the wireless healthcare measurement device 140 is to be associated and connected can be recognized by the wireless healthcare measurement device 140 through factory pre-configuration). In this case, a user needs to plug-in the dongle (e.g., the translation units 130) into the healthcare gateway device 110, and then the healthcare measurement device 140 associates and communicates with the healthcare gateway device 110 without further user intervention. Similarly, the wired devices #5 and #6 of the healthcare measurement devices 140 are operatively coupled to the healthcare gateway device 110 through the USB to Ethernet and USB to Firewire of the translation units 130 via the Ethernet and Firewire of the device communication modules 125 as shown in FIG. 1.

Figure 2:
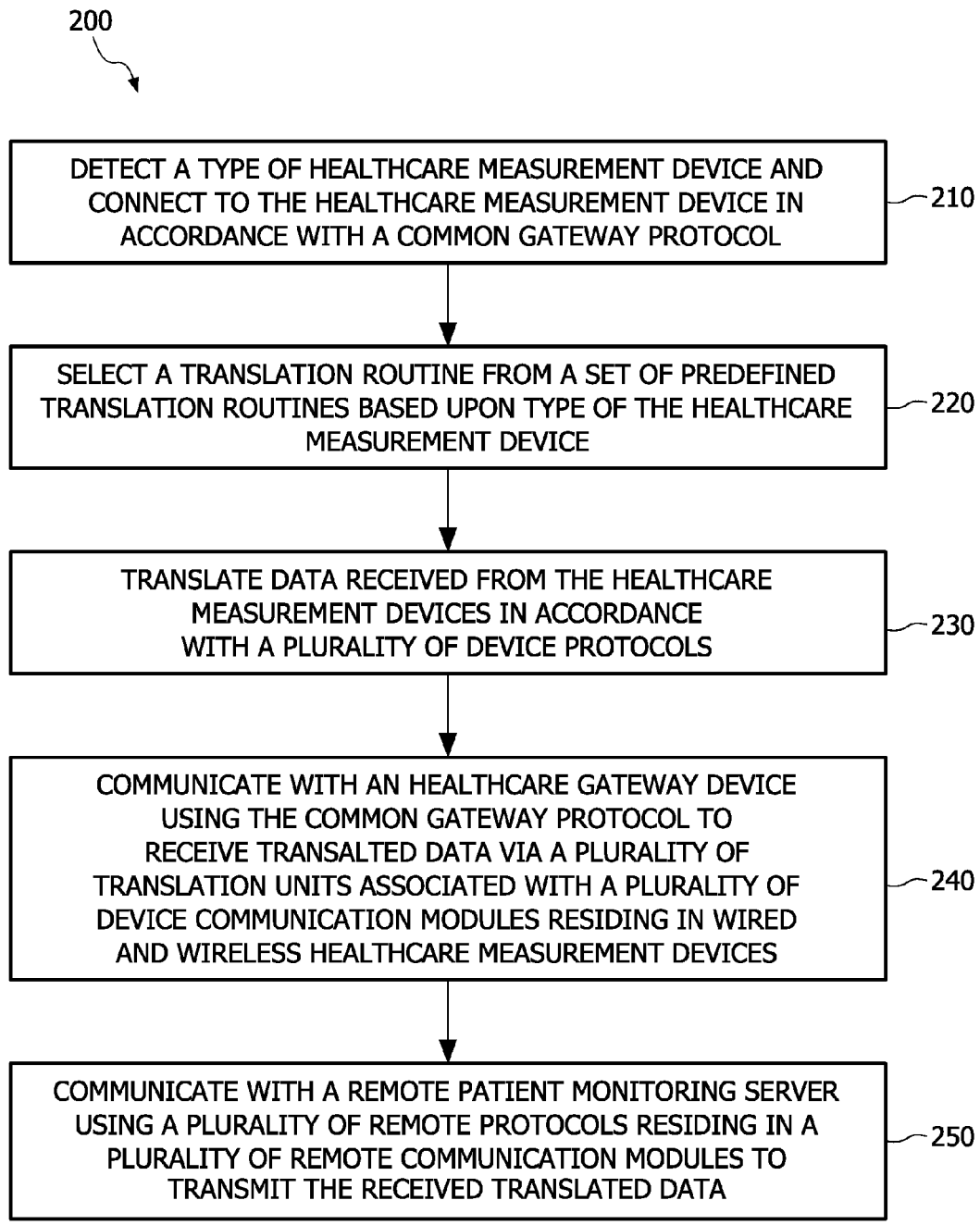
FIG. 2 is a flowchart for illustrating first exemplary method for operating the transport-agnostic gateway, shown in FIG. 1, in accordance with an embodiment of the invention.

FIG. 2 is a flowchart 200 for illustrating first exemplary method for operating the transport-agnostic gateway, shown in FIG. 1, in accordance with an embodiment of the invention. Particularly, FIG. 2 illustrates a method for effecting communication between a plurality of healthcare measurement devices 140 and a remote patient monitoring server 160. In some embodiments, an healthcare gateway device 110 is communicatively coupled between the plurality of the healthcare measurement devices 140 and the remote patient monitoring server 160.

In operation 210, a type of healthcare measurement device 140 is detected and the healthcare measurement device 140 is connected in accordance with a common gateway protocol. In operation 220, a translation routine is selected from a set of predetermined translation routines based upon the type of the healthcare measurement device 140. In operation 230, data received from the healthcare measurement devices 140 is translated in accordance with a plurality of device protocols. In these embodiments, data received from the healthcare measurement device 140 is translated in accordance with a plurality of device protocols into translated data adapted for the healthcare gateway device 110 in accordance with the common gateway protocol.

Further, information received from the healthcare gateway device 110 is translated in accordance with the common gateway protocol into translated information adapted for the one of the plurality of healthcare measurement devices 140 in accordance with one of the device protocols. In operation 240, the healthcare measurement device 140 is communicated with the healthcare gateway device 110 using a common gateway protocol to receive translated data via a plurality of translation units 130 associated with a plurality of device communication modules 125 residing in wired and wireless healthcare measurement devices 140. In operation 250, the healthcare gateway device 110 is communicated with the remote patient monitoring server 160 using a plurality of remote protocols residing in a plurality of remote communication modules 150 to transmit the received translated data.

Figure 3:
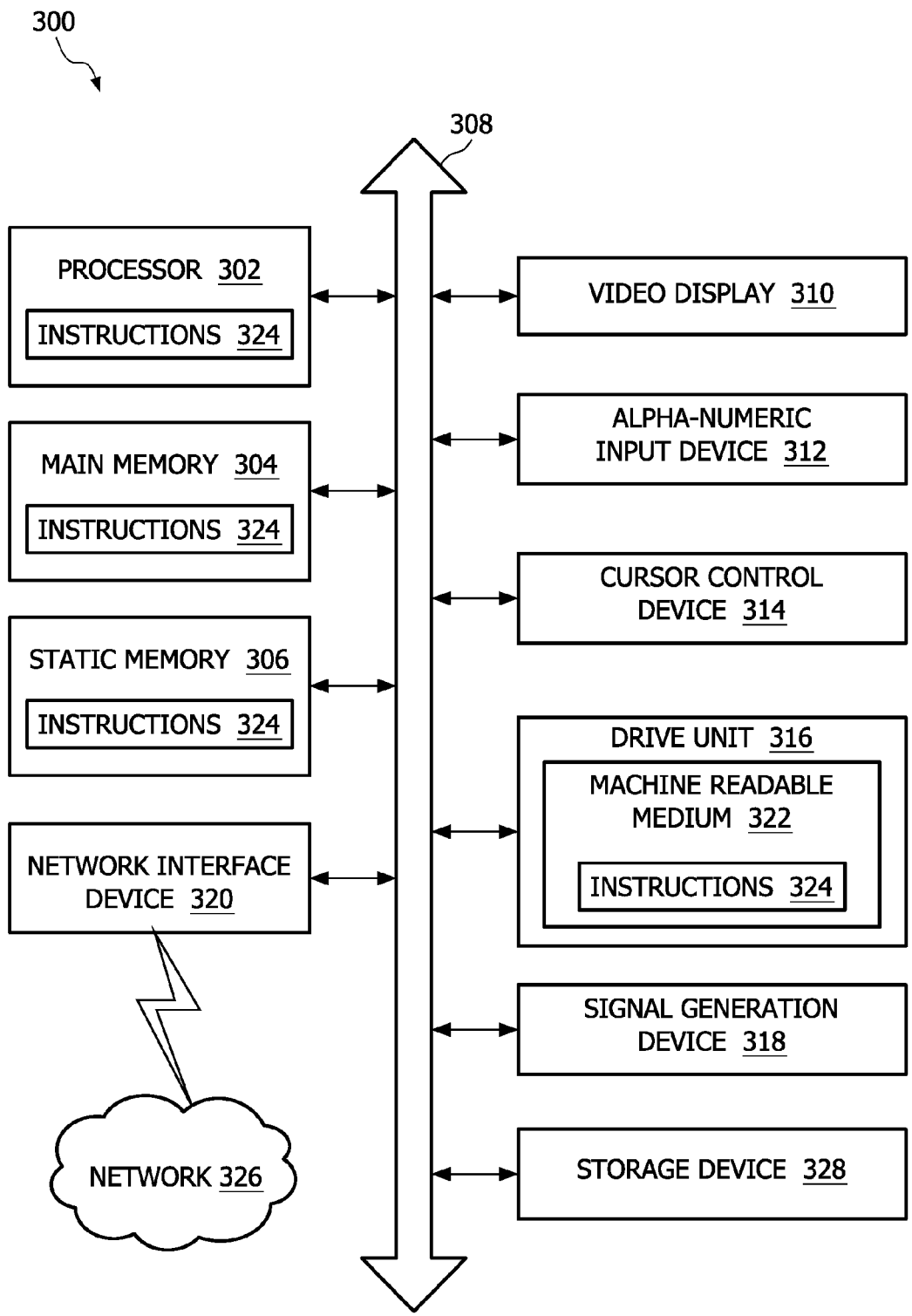
FIG. 3 is a diagrammatic system view of a data processing system in which any of the embodiments disclosed herein may be performed, according to one embodiment.

FIG. 3 illustrates a diagrammatic system view 300 of a data processing system in which any of the embodiments disclosed herein may be performed, according to one embodiment. Particularly, the diagrammatic system view of FIG. 3 illustrates a processor 302, a main memory 304, a static memory 306, a bus 308, a video display 310, an alpha-numeric input device 312, a cursor control device 314, a drive unit 316, a signal generation device 318, a network interface device 320, a machine readable medium 322, instructions 324, and a network 326.

The diagrammatic system view 300 may indicate a personal computer and/or a data processing system in which one or more operations disclosed herein are performed. The processor 302 may be a microprocessor, a state machine, an application specific integrated circuit, a field programmable gate array, etc. The main memory 304 may be a dynamic random access memory and/or a primary memory of a computer system. The static memory 306 may be a hard drive, a flash drive, and/or other memory information associated with the data processing system.

The bus 308 may be an inter-connection between various circuits and/or structures of the data processing system. The video display 310 may provide graphical representation of information on the data processing system. The alpha-numeric input device 312 may be a keypad, keyboard and/or any other input device of text (e.g., a special device to aid the physically handicapped). The cursor control device 314 may be a pointing device such as a mouse. The drive unit 316 may be a hard drive, a storage system, and/or other longer term storage subsystem.

The signal generation device 318 may be a bios and/or a functional operating system of the data processing system. The network interface device 320 may perform interface functions (e.g., code conversion, protocol conversion, and/or buffering) required for communications to and from the network 326 between a number of independent devices (e.g., of varying protocols). The machine readable medium 322 may provide instructions on which any of the methods disclosed herein may be performed. The instructions 324 may provide source code and/or data code to the processor 302 to enable any one or more operations disclosed herein.

A storage medium having instructions, that when executed by a computing platform, result in execution of a method of effecting communication between the healthcare measurement devices 140 and the remote patient monitoring server 160, in which the healthcare gateway device 110 is communicatively coupled between the healthcare measurement devices 140 and the remote patient monitoring server 160, including communicating with the healthcare gateway device 110 using a common gateway protocol to receive translated data via the translation units 130 associated with the device communication modules 125 residing in the wired and wireless healthcare measurement devices 140, and communicating with the remote patient monitoring server 160 using the remote protocols residing in the remote communication modules 150 to transmit the received translated data.

In some embodiments, communicating with the healthcare measurement devices 140 includes detecting the type of the healthcare measurement device 140 and connecting to the healthcare measurement device 140 in accordance with the common gateway protocol. The storage medium may have instructions to translate data received from the healthcare measurement devices 140 in accordance with the device protocols into translated data adapted for the healthcare gateway device 110 in accordance with the common gateway protocol.

Further, the storage medium may have instructions to translate information received from the healthcare gateway device 110 in accordance with the common gateway protocol into translated information adapted for the one of the healthcare measurement devices 140 in accordance with the one of the device protocols. In some embodiments, translating includes selecting a translation routine from a set of predefined translation routines based upon type of the healthcare measurement devices 140.

The above-described healthcare gateway device 110 supports multiple radio technologies, such as Bluetooth, Zigbee, etc., between the healthcare measurement devices 140 and the transport-agnostic gateway of the gateway communication modules 120. The above-described healthcare gateway device 110 equips the gateway with a single type of wired connection only (e.g. USB), and supplies dedicated pre-paired wireless dongles with each wireless device, that allows simple, secure association and subsequent connection of the healthcare measurement devices 140 with the healthcare gateway device 110, through simply plugging in the dongle into one of the standard wired gateway ports.

Also, the method may be in a form of a machine-readable medium embodying a set of instructions that, when executed by a machine, cause the machine to perform any method disclosed herein. It will be appreciated that the various embodiments discussed herein may not be the same embodiment, and may be grouped into various other embodiments not explicitly disclosed herein. In addition, it will be appreciated that the various operations, processes, and methods disclosed herein may be embodied in a machine-readable medium and/or a machine accessible medium compatible with a data processing system (e.g., a computer system), and may be performed in any order (e.g., including using means for achieving the various operations). Accordingly, the specification and drawings are to be regarded in an illustrative rather than a restrictive sense.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) each of the disclosed elements may be comprised of hardware portions (e.g., discrete electronic circuitry), software portions (e.g., computer programming), or any combination thereof.

What is claimed is:

1. A healthcare gateway device for effecting transport-agnostic communication between a plurality of healthcare measurement devices and a remote patient monitoring server, comprising:
   a plurality of gateway communication modules, each including:
      a plug and play port which uses a common gateway protocol to receive translated data;
      a translation unit connected to the plug and play port which receives data from a healthcare measurement device and translates the received data from a device protocol to the common gateway protocol and the translation unit includes at least one of a wired or a wireless port; and
   a plurality of remote communication modules, each including:
      a communication port communicatively coupled to the plurality of gateway communication modules to transmit the translated data to the remote patient monitoring server;
   wherein the plurality of remote communication modules are communicatively coupled to the plurality of gateway communication modules to send data to the remote patient monitoring server according to the common gateway protocol; and
   wherein the translation units translate the data to the common gateway protocol from the device protocols.

2. A healthcare gateway device for effecting transport-agnostic communication between a plurality of healthcare measurement devices and a remote patient monitoring server, comprising:
   a plurality of gateway communication modules, each including:
      a plug and play port which uses a common gateway protocol to receive translated data;
      a translation unit connected to the plug and play port which receives data from a healthcare measurement device and translates the received data from a device protocol to the common gateway protocol and the translation unit includes at least one of a wired or a wireless port; and
   a plurality of remote communication modules, each including:
      a communication port communicatively coupled to the plurality of gateway communication modules to transmit the translated data to the remote patient monitoring server;
   wherein the plurality of remote communication modules are communicatively coupled to the plurality of gateway communication modules to receive data from the remote patient monitoring server according to the common gateway protocol; and
   wherein the translation units translate the data from the common gateway protocol to the device protocols.

3. The healthcare gateway device of claim 1, wherein the healthcare measurement devices comprise devices selected from the group consisting of a weigh scale and a BP-meter, a glucometer, a thermometer, a heart rate sensor, an ECG sensor, an EEG sensor, an oximeter, a PT-INR sensor, a peak flow sensor, a spirometer, a respiration sensor, a passive infrared (PIR) motion sensor, a smoke detector, and an emergency button.

4. The healthcare gateway device of claim 3, wherein the common gateway protocol includes a USB protocol and the plug and play ports include USB ports.

5. The healthcare gateway device of claim 3, wherein the translation units are configured to use a plurality of device protocols selected from the group consisting of a USB protocol, an RS232 protocol, an IR protocol, an Ethernet protocol, a Fire Wire protocol, a Bluetooth protocol, a Zigbee protocol, an ULP Bluetooth protocol, and a Z-Wave protocol.

6. A system for effecting communication between a plurality of healthcare measurement devices and a remote patient monitoring server using an healthcare gateway device that uses a common gateway protocol, comprising:

a remote patient monitoring server;

a plurality of healthcare measurement devices each including a device communication module which transmits and receives data in accordance with a device protocol;

a healthcare gateway device which includes:

a plurality of remote communication modules communicatively coupled to the remote patient monitoring server via a plurality of remote protocols; and a plurality of gateway communication modules that use a common gateway protocol each module includes a plug and play port, and wherein the plurality of remote protocols are compliant with the common gateway protocol; and a translation unit, operatively connected to the plurality of device communication modules and to the plurality of gateway communication modules, for translating the data received from the plurality of wired and wireless healthcare measurement devices in accordance with the plurality of device protocols into translated data adapted for the healthcare gateway device in accordance with the common gateway protocol;

wherein the plurality of remote communication modules are communicatively coupled to the plurality of gateway communication modules to at least one of receive data from and send data to the remote patient monitoring server according to the common gateway protocol; and wherein the translation units translate the data between the common gateway protocol and the device protocols.

7. The system of claim 6, wherein the translation unit is further operative to translate information received from the healthcare gateway device in accordance with the common gateway protocol into translated information adapted for the plurality of wired and wireless healthcare measurement devices in accordance with the plurality of device protocols.

8. The system of claim 6, wherein the common gateway protocol includes a USB protocol, and the plug and play port includes a USB port.

9. The system of claim 6, wherein the plurality of device communication modules include peripheral detection and connection modules.

10. The system of claim 6, wherein the healthcare gateway device comprises devices selected from the group consisting of a personal computer, a settop box, a mobile phone, and a personal digital assistant.

11. The system of claim 6, wherein the plurality of device communication modules residing in the wired and wireless healthcare measurement devices comprise modules selected from the group consisting of a USB connection, an RS232 connection, an InfraRed (IR) connection, an Ethernet connection, a FireWire connection, a Bluetooth interface, a Wireless USB, a Zigbee interface, an Ultra Low Power (ULP) Bluetooth interface, and a Z-Wave interface.

* * * * *